(12) United States Patent
Dacosta et al.

(10) Patent No.: US 11,395,691 B2
(45) Date of Patent: *Jul. 26, 2022

(54) ALIGNMENT GUIDE APPARATUS, METHODS AND SYSTEMS

(71) Applicant: Paragon 28, Inc., Englewood, CO (US)

(72) Inventors: Albert Dacosta, Lone Tree, CO (US); Thomas Sangiovanni, Miami, FL (US)

(73) Assignee: Paragon 28, Inc., Englewood, CO (US)

( * ) Notice: Subject to any disclaimer, the term of this patent is extended or adjusted under 35 U.S.C. 154(b) by 327 days.

This patent is subject to a terminal disclaimer.

(21) Appl. No.: 16/450,505

(22) Filed: Jun. 24, 2019

(65) Prior Publication Data

US 2019/0307498 A1    Oct. 10, 2019

Related U.S. Application Data

(63) Continuation of application No. 15/948,759, filed on Apr. 9, 2018, now Pat. No. 10,327,829, which is a
(Continued)

(51) Int. Cl.
*A61B 17/80* (2006.01)
*A61B 17/88* (2006.01)
(Continued)

(52) U.S. Cl.
CPC .......... *A61B 17/8897* (2013.01); *A61B 17/17* (2013.01); *A61B 17/56* (2013.01);
(Continued)

(58) Field of Classification Search
CPC ... A61B 17/80; A61B 17/808; A61B 17/8872; A61B 2017/90
See application file for complete search history.

(56) References Cited

U.S. PATENT DOCUMENTS

| 2,526,959 A | 10/1950 | Lorenzo |
| 3,709,219 A | 1/1973 | Halloran |
| (Continued) | | |

FOREIGN PATENT DOCUMENTS

| EP | 0617927 | 10/1994 |
| EP | 1273271 | 8/2007 |
| (Continued) | | |

OTHER PUBLICATIONS

Partial Supplementary European Search Report issued in European Patent Application No. 18777784.2, dated Jan. 14, 2021, 13 pages.
(Continued)

*Primary Examiner* — Nicholas W Woodall
(74) *Attorney, Agent, or Firm* — Heslin Rothenberg Farley & Mesiti P.C.; Jacquelyn A. Graff, Esq.

(57) ABSTRACT

The present invention discloses an alignment guide apparatus, system, and method. The alignment guide apparatus includes a body, a fixation insert, a guide pin, and a screw. The body may include an arm with a first end and a second end, an attachment portion at the first end, and an alignment portion at the second end. The fixation insert may be configured to pass through the attachment portion and the guide pin may be configured to pass through the alignment portion. The screw may be configured to engage the guide pin. The alignment system may include a bone plate, an alignment guide, a screw, at least one first fastener, and at least one second fastener. A method for moving a joint is also disclosed.

19 Claims, 17 Drawing Sheets

Related U.S. Application Data continuation of application No. 14/655,943, filed as application No. PCT/US2014/045441 on Jul. 3, 2014, now Pat. No. 9,936,995, which is a continuation-in-part of application No. PCT/US2013/077211, filed on Dec. 20, 2013.

(60) Provisional application No. 61/746,928, filed on Dec. 28, 2012.

(51) Int. Cl.
    *A61B 17/17* (2006.01)
    *A61B 17/56* (2006.01)
    *A61B 17/90* (2006.01)

(52) U.S. Cl.
    CPC ...... *A61B 17/8019* (2013.01); *A61B 17/1717* (2013.01); *A61B 17/1728* (2013.01); *A61B 17/90* (2021.08)

(56) References Cited

U.S. PATENT DOCUMENTS

| | | | |
|---|---|---|---|
| 4,483,334 A | 11/1984 | Murray | |
| 4,790,302 A | 12/1988 | Colwill | |
| 5,098,435 A | 3/1992 | Stednitz | |
| 5,350,380 A | 9/1994 | Goble | |
| 5,352,228 A | 10/1994 | Kummer | |
| 5,429,641 A | 7/1995 | Gotfried | |
| 5,458,602 A | 10/1995 | Goble | |
| 6,342,057 B1 | 1/2002 | Brace | |
| 6,692,496 B1 | 2/2004 | Wardlaw | |
| 7,011,665 B2 | 3/2006 | Null | |
| 7,316,687 B2 | 1/2008 | Aikins | |
| 7,785,326 B2 | 8/2010 | Green | |
| 7,819,877 B2 | 10/2010 | Guzman | |
| 8,206,389 B2 | 6/2012 | Huebner | |
| 8,231,627 B2 | 7/2012 | Huebner | |
| 8,337,503 B2 | 12/2012 | Lian | |
| 8,535,355 B2 | 9/2013 | Prasad | |
| 9,044,250 B2 | 6/2015 | Olsen et al. | |
| 9,161,796 B2 | 10/2015 | Chiodo | |
| 9,241,744 B2 | 1/2016 | Blake | |
| 9,421,103 B2 | 8/2016 | Jeng et al. | |
| 2003/0009217 A1 | 1/2003 | McKernan | |
| 2004/0102776 A1* | 5/2004 | Huebner | A61B 17/8052 606/281 |
| 2004/0102777 A1* | 5/2004 | Huebner | A61B 17/1782 606/281 |
| 2004/0181221 A1 | 9/2004 | Huebner | |
| 2005/0033301 A1 | 2/2005 | Lombardo | |
| 2005/0059968 A1 | 3/2005 | Grant | |
| 2005/0234472 A1 | 10/2005 | Huebner | |
| 2006/0189996 A1 | 8/2006 | Orbay | |
| 2007/0173843 A1 | 7/2007 | Matityahu | |
| 2007/0225714 A1 | 9/2007 | Gradl | |
| 2007/0239168 A1 | 10/2007 | Kuenzi | |
| 2007/0265634 A1 | 11/2007 | Weinstein | |
| 2007/0270850 A1* | 11/2007 | Geissler | A61B 17/15 606/326 |
| 2008/0015590 A1* | 1/2008 | Sanders | A61B 90/94 606/86 A |
| 2008/0091197 A1 | 4/2008 | Coughlin | |
| 2008/0188852 A1 | 8/2008 | Matityahu | |
| 2009/0036931 A1 | 2/2009 | Pech | |
| 2009/0088767 A1 | 4/2009 | Leyden | |
| 2009/0093849 A1 | 4/2009 | Grabowski | |
| 2010/0087824 A1 | 4/2010 | Collazo | |
| 2010/0121324 A1 | 5/2010 | Tyber | |
| 2011/0046681 A1 | 2/2011 | Prandi et al. | |
| 2011/0144647 A1 | 6/2011 | Appenzeller | |
| 2011/0144700 A1 | 6/2011 | Konieczynski | |
| 2011/0218576 A1 | 9/2011 | Galm | |
| 2011/0224734 A1* | 9/2011 | Schelling | A61B 17/7079 606/286 |
| 2011/0264149 A1 | 10/2011 | Pappalardo | |
| 2011/0270319 A1 | 11/2011 | Sheffer | |
| 2011/0282397 A1 | 11/2011 | Richter | |
| 2012/0078252 A1 | 3/2012 | Huebner | |
| 2012/0209268 A1 | 8/2012 | Overes | |
| 2012/0253347 A1 | 10/2012 | Murashko, Jr. | |
| 2012/0303038 A1 | 11/2012 | Durante | |
| 2012/0316562 A1* | 12/2012 | Costa | A61B 17/8066 606/71 |
| 2013/0046311 A1 | 2/2013 | Blake et al. | |
| 2013/0150903 A1 | 6/2013 | Vincent | |
| 2013/0172942 A1 | 7/2013 | Lewis et al. | |
| 2014/0066996 A1 | 3/2014 | Price et al. | |
| 2014/0180348 A1 | 6/2014 | Thoren et al. | |
| 2015/0032168 A1 | 1/2015 | Orsak et al. | |
| 2015/0150683 A1 | 6/2015 | Donner et al. | |
| 2015/0182267 A1 | 7/2015 | Wolf et al. | |
| 2015/0238227 A1 | 8/2015 | Singh et al. | |
| 2015/0245923 A1 | 9/2015 | Abdou | |
| 2015/0289904 A1 | 10/2015 | Thoren et al. | |
| 2016/0030064 A1 | 2/2016 | Dacosta et al. | |
| 2016/0135858 A1 | 5/2016 | Dacosta et al. | |
| 2016/0235414 A1 | 8/2016 | Hatch et al. | |
| 2016/0242791 A1 | 8/2016 | Fallin et al. | |
| 2016/0310191 A1 | 10/2016 | Seykora | |
| 2016/0324552 A1 | 11/2016 | Baker et al. | |
| 2016/0354128 A1 | 12/2016 | Jeng | |
| 2017/0000534 A1 | 1/2017 | Medoff | |
| 2017/0056031 A1 | 3/2017 | Awtrey et al. | |
| 2017/0216043 A1 | 8/2017 | Surma et al. | |

FOREIGN PATENT DOCUMENTS

| | | |
|---|---|---|
| EP | 2745786 | 6/2014 |
| EP | 3023068 | 5/2016 |
| FR | 3030221 | 6/2016 |
| JP | 04250156 | 9/1992 |
| JP | 2009112954 | 5/2009 |
| WO | 1994015556 | 7/1994 |
| WO | 2005089660 | 9/2005 |
| WO | 2009052294 | 4/2009 |
| WO | 2012103335 | 8/2012 |
| WO | 2012106477 | 8/2012 |
| WO | 2013009574 | 1/2013 |
| WO | 2014105750 | 7/2014 |
| WO | 2015094409 | 6/2015 |
| WO | 2015138542 | 9/2015 |
| WO | 2017011656 | 1/2017 |
| WO | 2018157170 | 8/2018 |

OTHER PUBLICATIONS

Extended European Search Report issued in European Patent Application No. 18757770.5, dated Mar. 9, 2021, 10 pages.

Extended European Search Report issued in European Patent Application No. 18758239.0, dated Apr. 8, 2021, 12 pages.

Extended European Search Report issued in European Patent Application No. 18831633.5, dated Apr. 16, 2021, 10 pages.

Extended European Search Report issued in European Patent Application No. 18777784.2, dated Apr. 16, 2021, 11 pages.

Partial Supplementary European Search Report issued in European Patent Application No. 18757770.5 dated Dec. 3, 2020, 11 pages.

Partial Supplementary European Search Report issued in European Patent Application No. 18758239.0, dated Dec. 10, 2020, 11 pages.

European Communication Pursuant to Article 94(3) EPC (Office Action) for EP Application No. 18201132.0 dated Feb. 12, 2021, 5 pages.

Budny et al. "Naviculocuneiform Arthrodesis," Clinics in Podiatric Medicine and Surgery, vol. 24, pp. 753-763, Oct. 2007.

International Search Report and Written Opinion of the International Searching Authority for PCT/US2013/077211, dated Apr. 3, 2014, 12 pages.

Kamat et al. "Laparoscopic extraction of fractured Kirschner wire from the pelvis," Journal of Minimal Access Surgery, vol. 10, No. 2, pp. 97-98, Jun. 2014.

(56) References Cited

OTHER PUBLICATIONS

International Search Report and Written Opinion of the International Searching Authority for PCT/US2014/045441, dated Nov. 25, 2014, 8 pages.
International Preliminary Report on Patentability for PCT/US2013/077211, dated Jun. 30, 2015, 8 Pages.
International Preliminary Report on Patentability for PCT/US2014/045441, dated Jun. 21, 2016, 7 Pages.
Extended European Search Report issued in European Patent Application No. 13869787.5, dated Jul. 18, 2016, 6 pages.
Extended European Search Report issued in European Patent Application No. 15195121.7, dated Jul. 28, 2016, 26 pages.
International Search Report and Written Opinion issued in corresponding PCT Application No. PCT/US2017/058168, dated Jan. 8, 2018, 8 pages.
International Search Report and Written Opinion issued in corresponding PCT Application No. PCT/US2018/020046, filed May 14, 2018, 11 pages.
International Search Report and Written Opinion of the International Searching Authority for PCT/US2018/020053, dated May 30, 2018, 11 pages.
International Search Report and Written Opinion of the International Searching Authority for PCT/US2018/025443, dated Aug. 1, 2018, 12 pages.
International Search Report and Written Opinion of the International Searching Authority for PCT/US2018/041657, dated Nov. 14, 2018, 21 pages.
Extended European Search Report (EESR) for EP Application No. 17863986.0, dated Sep. 15, 2020 (13 pages).

\* cited by examiner

ALIGNMENT GUIDE APPARATUS, METHODS AND SYSTEMS

CROSS-REFERENCE TO RELATED APPLICATIONS

This application is a continuation of U.S. application Ser. No. 15/948,759 filed Apr. 9, 2018, which will issue as U.S. Pat. No. 10,327,829 on Jun. 25, 2019, which is a continuation of U.S. application Ser. No. 14/655,943 filed Jun. 26, 2015, which issued as U.S. Pat. No. 9,936,995 on Apr. 10, 2018, which is a National Stage application based on International Application No. PCT/US2014/045441 filed on Jul. 3, 2014, published as WO 2015/094409 A1 on Jun. 25, 2015. This application also claims priority benefit to International application No. PCT/US2013/077211 filed Dec. 20, 2013, published as WO 2014/105750, which claims priority benefit under 35 U.S.C. § 119(e) of U.S. provisional application No. 61/746,928 filed Dec. 28, 2012, which are incorporated herein by reference in their entireties.

FIELD OF THE INVENTION

The present invention relates generally to the field of orthopedics related to a bone plate alignment guide apparatus', systems, and methods for using the bone plate alignment guide apparatus.

SUMMARY OF THE INVENTION

The present invention is directed toward devices, methods and systems for aligning and securing an orthopedic bone plate for compression of a joint.

In one aspect, provided herein is a bone plate alignment guide apparatus. The bone plate alignment guide apparatus may include a body. The body may include an arm with a first end and a second end, an attachment portion at the first end, and an alignment portion at the second end. The bone plate alignment guide apparatus may also include a fixation insert configured to pass through the attachment portion and a guide pin configured to pass through the alignment portion. The bone plate alignment guide apparatus may also include a screw configured to engage the guide pin.

In another aspect, provided herein is a bone plate alignment system. The bone plate alignment system includes a bone plate, a bone plate alignment guide, a screw, at least one first fastener, and at least one second fastener. The bone plate of the system includes a first end, a second end, and an intermediate portion connecting the first end and the second end. The bone plate may include at least one through hole in the first end, at least one through hole in the second end, and at least one opening between the first end and the second end. The bone plate alignment guide of the system includes a body including an arm with a first end and a second end, an attachment portion at the first end, and an alignment portion at the second end. The bone plate alignment guide also includes a fixation insert configured to pass through the attachment portion and a guide wire configured to pass through the alignment portion. The fixation insert couples to the at least one opening of the bone plate. The system may also include a screw configured to engage the guide wire during insertion into at least one portion of bone. The system also includes at least one first fastener for insertion through the at least one through hole on the first end of the bone plate and into a first portion of bone. The system may also include at least one second fastener for insertion through the at least one through hole on the second end of the bone plate and into a second portion of bone.

In yet another aspect, provided herein is a method for moving a joint. The method including preparing the joint and obtaining a bone plate alignment guide apparatus. The bone plate alignment guide apparatus may include a body, a fixation insert, a guide pin, and a screw. The body includes an arm with a first end and a second end, an attachment portion at the first end, and an alignment portion at the second end. The fixation insert is configured to engage the attachment portion. The guide pin is configured to pass through the alignment portion. The screw is configured to engage the guide pin. The method may also include aligning a bone plate on the joint and inserting at least one first temporary fixation pin to secure the bone plate to a first bone of the joint. The method may further include inserting at least one second temporary fixation pin to secure the bone plate to a second bone of the joint. The method may also include attaching the bone plate alignment guide apparatus to the bone plate in a desired position relative to the joint. In addition, the method may also include inserting the guide pin across the joint through the alignment portion of the body of the bone plate alignment guide apparatus and inserting the screw over the guide pin to move the joint. The method may further include securing the bone plate to the first bone and the second bone of the joint and removing the bone plate alignment guide apparatus. Further, the method may include closing the incision in the patient.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the invention.

DETAILED DESCRIPTION FOR CARRYING OUT THE INVENTION

Figure 1:
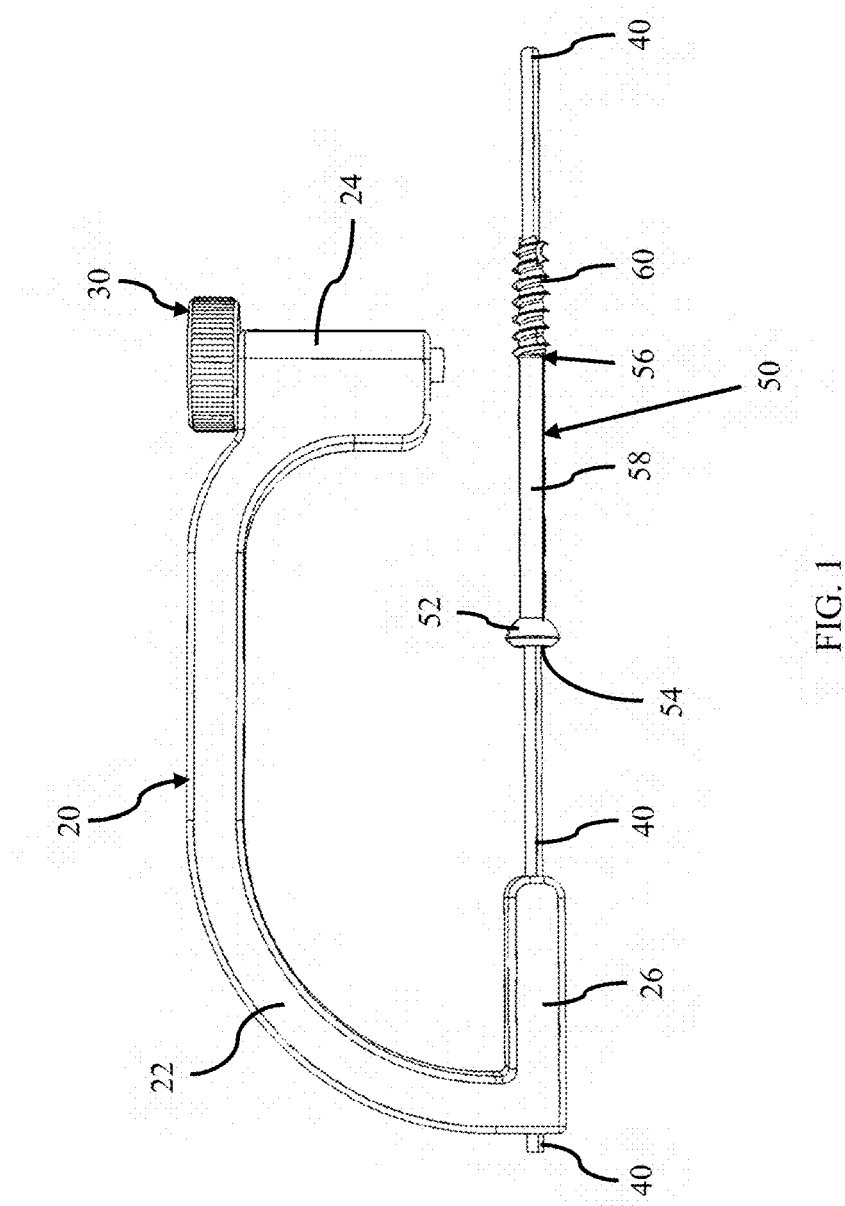
FIG. 1 is a side view of a bone plate alignment guide apparatus, in accordance with an aspect of the present invention.
Figure 2:
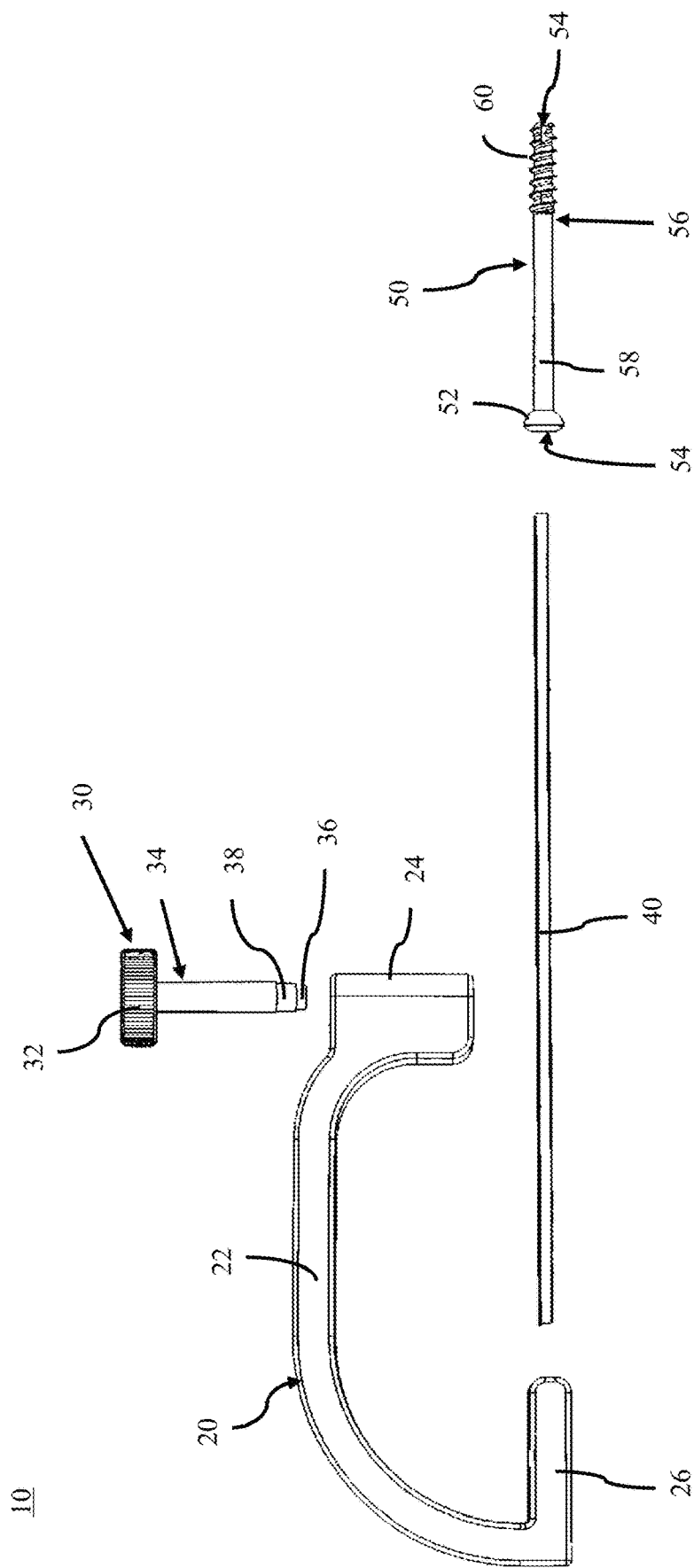
FIG. 2 is an exploded side view of the bone plate alignment guide apparatus of FIG. 1, in accordance with an aspect of the present invention.

Generally stated, disclosed herein is an embodiment of a bone plate alignment guide apparatus. Further, a surgical method for using the bone plate alignment guide apparatus is discussed.

In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of an implant nearest the torso, while "distal" indicates the portion of the implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

Referring to the drawings, wherein like reference numerals are used to indicate like or analogous components throughout the several views, and with particular reference to FIGS. 1-5, there is illustrated an exemplary embodiment bone plate alignment guide apparatus 10. The bone plate alignment guide apparatus 10 includes a body 20, a fixation insert 30, a guide wire or pin 40, and a compression or lag screw 50. The body 20 may include an arm 22 with an attachment portion 24 at a first end and an alignment portion 26 at a second end. The arm 22 may be configured to position the through hole of the attachment portion generally perpendicular to the at least one through hole of the alignment portion, as shown in FIGS. 1-4. The arm 22 may be arcuate, curved, angled, and the like. The fixation insert 30 may include a knob portion 32 and a shaft portion 34 with an alignment portion or alignment member 36 and a threaded section 38 for engaging the bone plate 80. The guide pin 40 may be, for example, a pin, k-wire or the like. The compression screw 50 may include a head portion 52 with a through hole 54 extending from the proximal end to the distal end of the screw 50 and a shank portion 56 extending away from the head portion 52 with a smooth upper portion 58 and a threaded portion 60 on the distal end of the screw 50.

Figure 3:
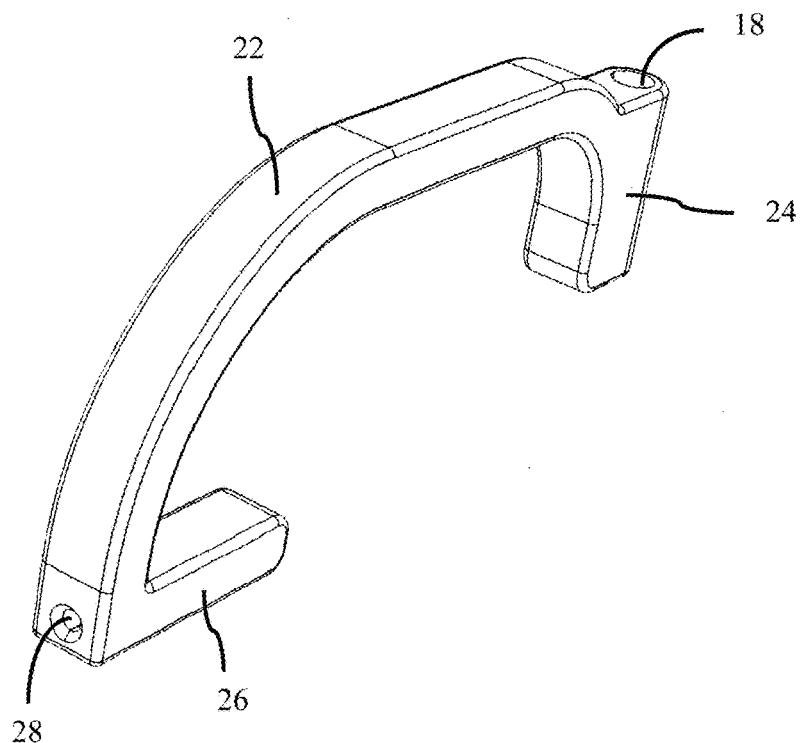
FIG. 3 is an end perspective view of the alignment guide of the bone plate alignment guide apparatus of FIG. 1, in accordance with an aspect of the present invention.
Figure 4:
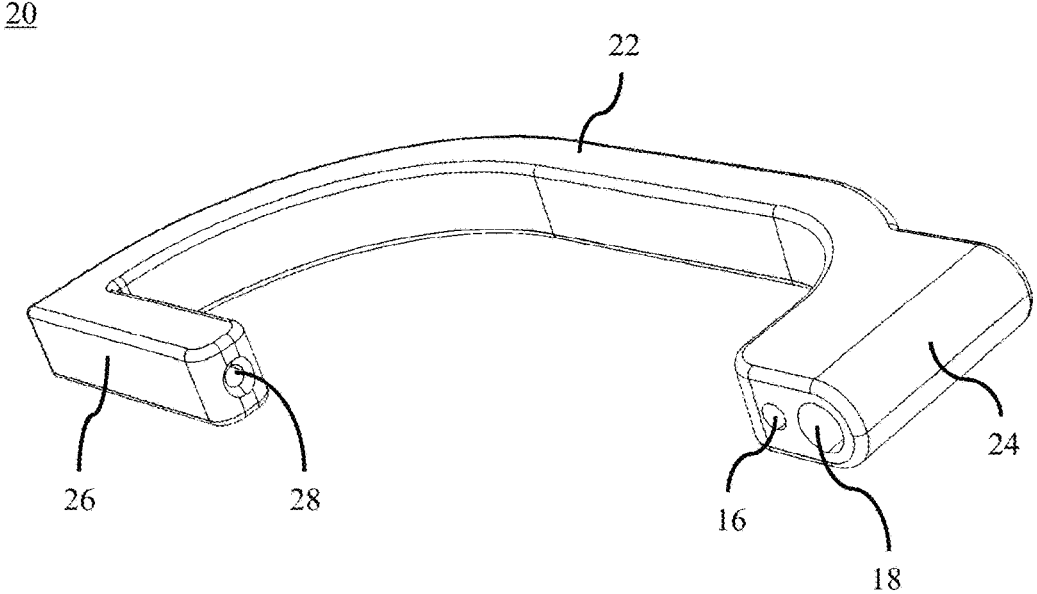
FIG. 4 is a bottom perspective view of the alignment guide of FIG. 3, in accordance with an aspect of the present invention.

As seen in FIGS. 3 and 4, the body 20 may also include a through hole 18 in the attachment portion 24 of the body 20 and a through hole 28 in the alignment portion 26 of the body 20. The body 20 may also include an opening 16 in the attachment portion 24 for inserting an alignment post or pin which may also engage the plate 80 for positioning the bone plate alignment guide apparatus 10 on the bone plate 80, as shown in FIG. 4.

Figure 5:
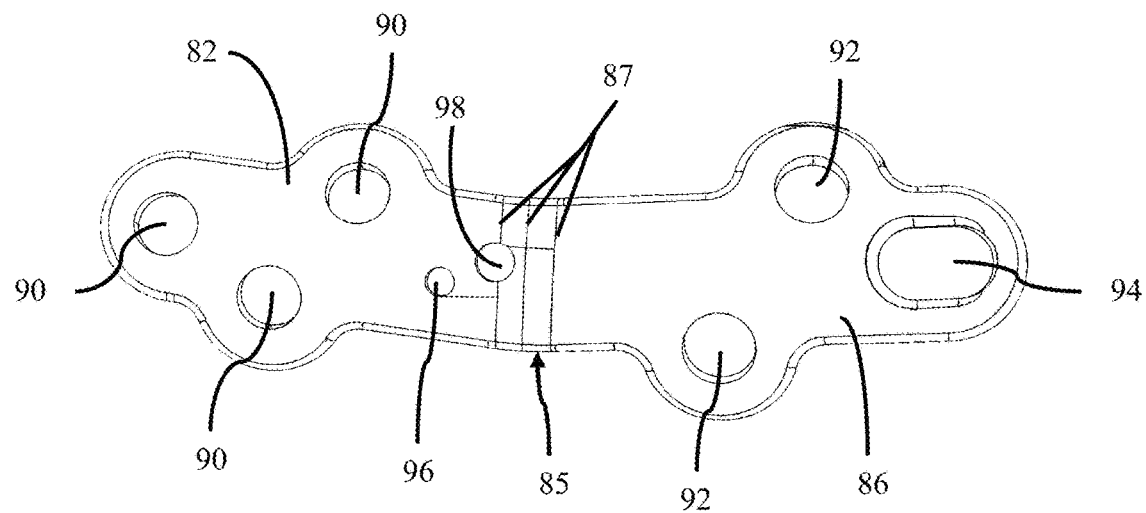
FIG. 5 is a top view of a bone plate for use with the bone plate alignment guide apparatus of FIG. 1, in accordance with an aspect of the present invention.
Figure 6:
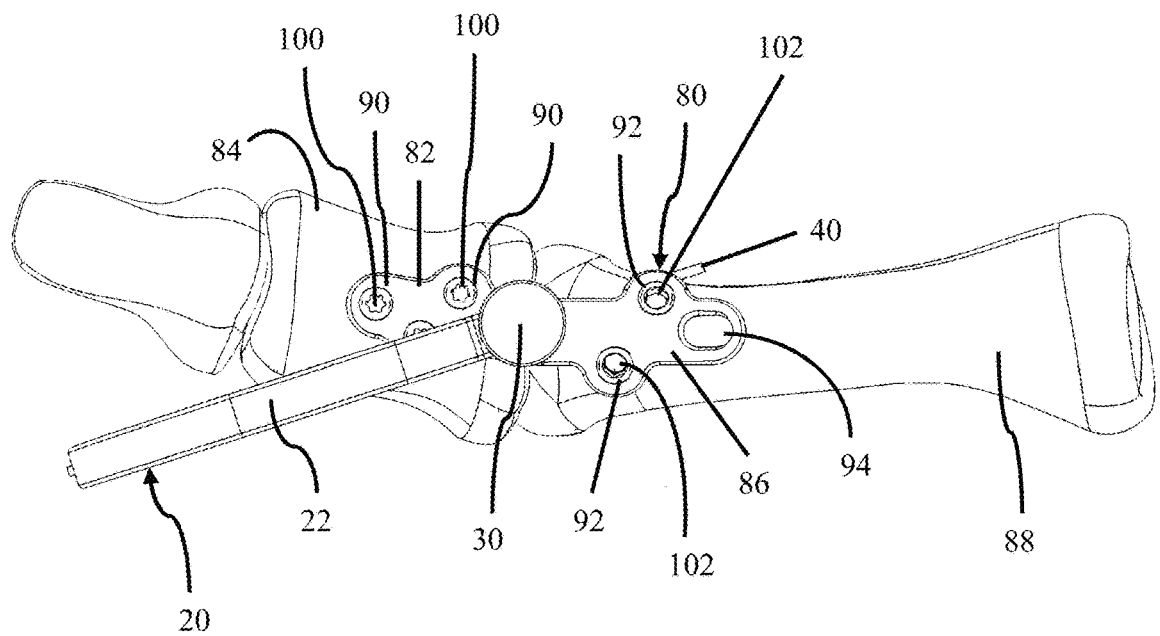
FIG. 6 is a top view of the bone plate alignment guide of FIG. 1 being used to insert a fastener into a patient's bones, in accordance with an aspect of the present invention.

Referring now to FIGS. 5 and 6, the bone plate 80 may include a first end 82 for attachment to a first bone 84 and a second end 86 for attachment to a second bone 88. The first end 82 may be connected to the second end 86 of the bone plate 80 by an intermediate member or portion 85. The bone plate 80 may also include at least one through hole 90 on the first end 82 of the plate 80 and at least one through hole 92 and a compression slot 94 on the second end 86 of the plate 80. The at least one through hole 90 may be used to insert fasteners, for example, fixation screws or bone screws 100 into the first bone 84, for example, the distal bone. The at least one through hole 92 may be used to insert fasteners, for example, fixation screws or bone screws 102 into the second bone 88, for example, the proximal bone. The compression slot 94 may allow for insertion of a fastener which may translate within the slot 94 while the distal and proximal bones 84, 88 are moved or compressed. The plate 80 may also include a first opening 96 for receiving the alignment post or pin (Not Shown). The alignment post or pin may also engage the opening 16 in the attachment portion 24 of the body 20 to align the alignment guide apparatus 10 with the plate 80. The plate 80 may also include a second opening 98 which the through hole 18 may align with to allow for insertion of the alignment portion 36 and the threaded section 38 of the fixation insert 30. The first opening 96 may be offset from the second opening 98 along the longitudinal axis of the plate 80 by, for example, approximately 30 to 40 degrees and more preferably by approximately 35 degrees. The intermediate member 85 may include at least one alignment marking 87 for use in alignment of the plate 80 with respect to the joint space.

Figure 7:
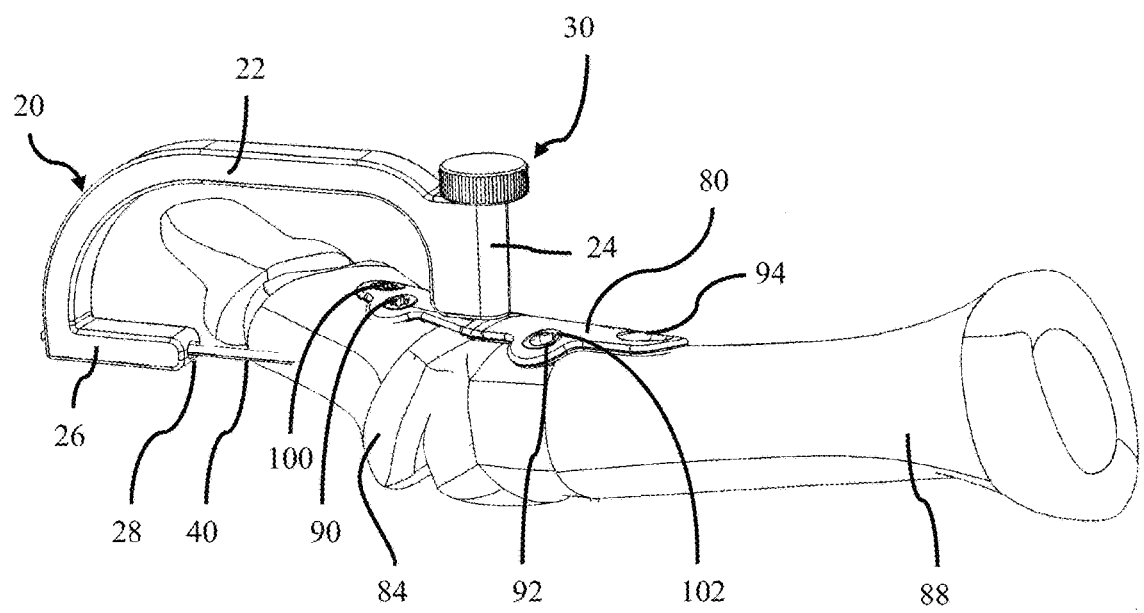
FIG. 7 is a side view of the bone plate alignment guide of FIG. 1 being used to align the bone plate of FIG. 5 onto a patient's bones, in accordance with an aspect of the present invention.
Figure 8:
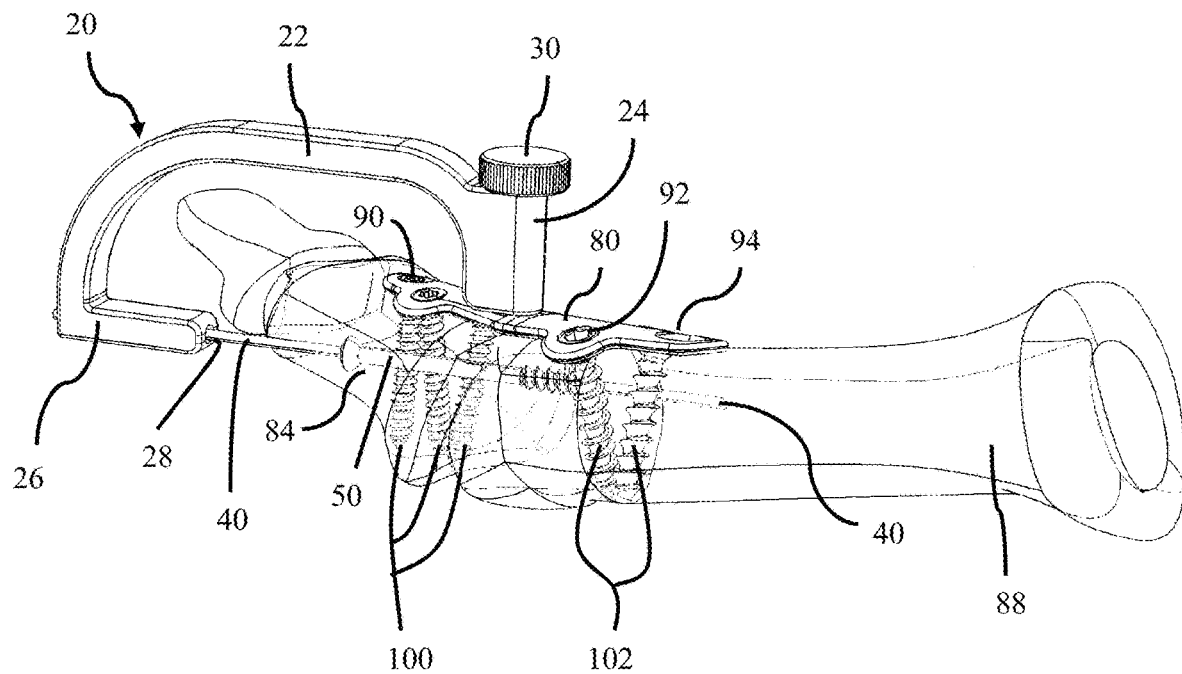
FIG. 8 is the side view of FIG. 7 with transparent bones showing the guide pin, compression screw and fasteners inserted into the patient's bones, in accordance with an aspect of the present invention.
Figure 9:
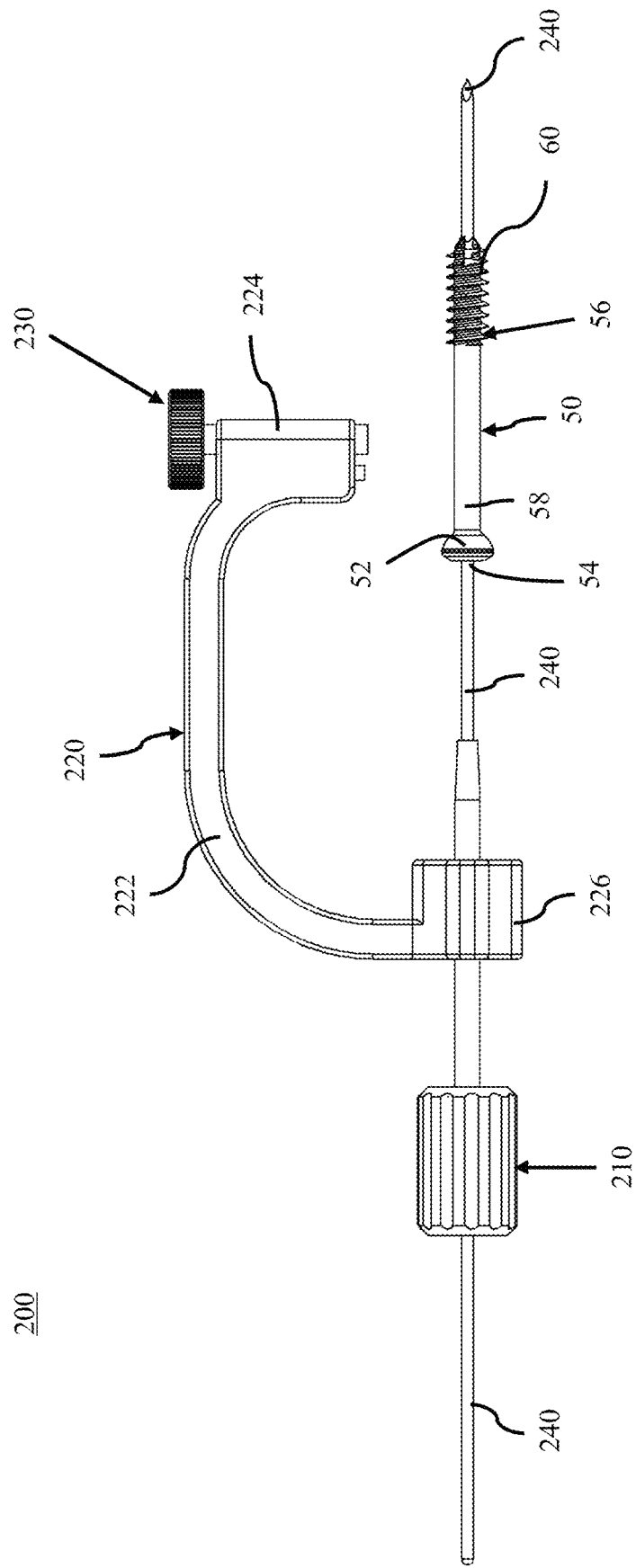
FIG. 9 is a side view of a bone plate alignment guide apparatus, in accordance with an aspect of the present invention.

Referring now to FIGS. 6-8, the method of using the bone plate alignment guide apparatus 10 includes opening the patient where joint compression and fixation is needed, for example a patient's foot, and preparing the joint for fixation. The joint may be, for example, a metatarsal-phalangeal joint or any other joint or bones where compression and fixation is necessary. The method may also include aligning the bone plate 80 on the distal and proximal bones 84, 88 by referring to the intermediate portion 85 of the plate 80 and aligning the at least one alignment marking 87 over the joint space. The method may further include inserting, for example, temporary fixation pins, olive wires, k-wires or the like may be inserted to hold the bone plate 80 in position on the distal and proximal bones 84, 88. In the preferred embodiment, olive wires or other temporary fixation mechanisms which hold the plate 80 to the bones 84, 88 during compression and fixation are used. The physician may then use fluoroscopy to confirm that the plate 80 is positioned on the distal and proximal bones 84, 88 in the desired position. The bone plate alignment guide apparatus 10 may then be attached to the bone plate 80.

As shown in FIGS. 4-5, the alignment guide apparatus 10 may be attached to the bone plate 80 by first inserting an alignment pin or post (Not Shown) into the first opening 96 on the plate 80 and then aligning the opening 16 in the body 20 with the alignment post or pin inserted into the plate 80. Once the alignment post or pin is inserted into the first opening 96 in the plate 80 and the opening 16 in the body 20, then the shaft portion 34 of the fixation insert 30 may be inserted into through hole 18 in the body 20 of the alignment guide apparatus 10 to engage the second opening 98 in the plate 80.

Alternatively, the fixation insert 30 may be inserted into the through hole 18 and used to align the body 20 with the second opening 98 on the plate 80, without using an alignment pin or post. The plate 80 may, for example, include at least two positive stops (Not Shown) on the plate 80, providing the surgeon minimal amount of pivot of the body 20 of the alignment guide apparatus 10 about the second opening 98 of the plate 80.

Another alternative embodiment of the plate 80, may, for example, include having a plurality of first openings 96 for aligning the guide body 20 for insertion of the compression screw 50 without interfering with another fastener 100, 102. In still another alternative plate embodiment, the plate 80 may, for example, include at least two alignment markings 87 on the plate 80, which the surgeon may use to align the guide body 20 in a position to avoid the compression screw 50 and the fasteners 100, 102 from coming into contact with each other. Additional alignment mechanisms for aligning the guide body 20 to ensure the fasteners 100, 102 and the compression screw 50 do not come in contact are also contemplated.

The guide body 20 may then be aligned in the desired position relative to distal and proximal bones 84, 88 and the fixation insert 30 tightened to secure the body 20 of the alignment guide apparatus 10 to the plate 80 in the desired position. After securing the guide body 20 of the alignment guide apparatus 10 to the plate 80 using any of the above described methods, the guide pin 40, for example, a k-wire, may be inserted in through hole 28 and into the distal and proximal bones 84, 88. Next, a drill may be inserted into the through hole 28 of the body 20 over the guide wire 40 to drill an opening in the distal and proximal bones 84, 88 for inserting the compression screw 50. The drill may then be removed from the through hole 28 and a compression screw 50 may be inserted into the through hole 28 over the guide wire 40. As the compression screw 50 is inserted over the guide wire 40 and into the distal and proximal bones 84, 88, the bones 84, 88 are pulled and compressed together.

Once the physician reaches a desired amount of movement or compression between the distal and proximal bones 84, 88, the temporary fixation means, for example, pins, olive wires, k-wires or the like, may be removed from the distal end 82 of the plate 80. Then the fasteners 100 may be inserted into the at least one through hole 90, for example, in the depicted embodiments, there are three through holes 90, in the plate 80 and into the distal bone 84, for example, the proximal phalange. The method may also include removing the temporary fixation means, for example, pins, olive wires, k-wires or the like from the proximal end 86 of the plate 80 and the fasteners 102 may be inserted into the at least one through hole 92, for example, in the depicted embodiments there are two through holes 92, in the plate 80 and into the proximal bone 88, for example, the metatarsal. Next, the position of the distal and proximal bones 84, 88 may be checked using, for example, fluoroscopy. If the bones 84, 88 are in the desired position, then the physician may remove the alignment guide apparatus 10, by first removing the guide wire 40, then loosening the fixation insert 30 to disengage the second opening 98 in the plate 80 and remove the fixation insert 30 and the body 20 of the alignment guide apparatus 10 from the patient's bones 84, 88. Finally, the patient's incision may be closed.

Referring to FIGS. 1-8, a bone plate alignment system may include, for example, a bone plate 80, an alignment guide apparatus 10, at least one first fastener 100, and at least one second fastener 102. The bone plate 80 may, for example, be of the type described above with reference to FIG. 5. The alignment guide apparatus 10 may, for example, be of the type described above with reference to FIGS. 1-4 and may include a body 20, a fixation insert 30, a guide pin 40, and a compression screw 50. The fasteners 100, 102 may be, for example, the type described above with reference to FIGS. 6-8. The bone plate alignment system may enable a physician or surgeon to use the bone plate 80 to pivot the alignment guide apparatus 10 into a position to allow for accurate insertion of the compression screw 50 relative to the bone plate 80. By enabling the surgeon to align and insert the compression screw 50 based on the orientation of the bone plate 80, the compression screw 50 may be inserted to, for example, avoid the positions where the fasteners 100, 102 will be inserted or where the fasteners 100, 102 are already positioned. The bone plate alignment system may be used, for example, to secure a bone plate 80 over a joint or at least two portions of a fractured bone.

Another embodiment bone plate alignment guide apparatus 200 is shown in FIGS. 9-12. The bone plate alignment guide apparatus 200 may include a body or alignment guide 220, a fixation member 230, a guide pin tissue protector 210, a guide wire or pin 240, and a fastener 50. The fixation member 230 may include a knob portion 232 and a shaft portion 234 with an engagement portion 236 for engaging the bone plate 80. The guide wire 240 may be, for example, a pin, k-wire, olive wire, or the like. The fastener 50 may be of the type described above with reference to FIGS. 1-5 and may be, for example, a compression screw, lag screw, headless screw, or a solid screw. The fastener 50 may include a head portion 52 with a through hole 54 extending from a first end to a second end of the fastener 50 and a shaft portion 56 extending away from the head portion 52. The shaft portion 56 may include a smooth upper portion 58 and a threaded portion 60 on the second end of the fastener 50.

Figure 10:
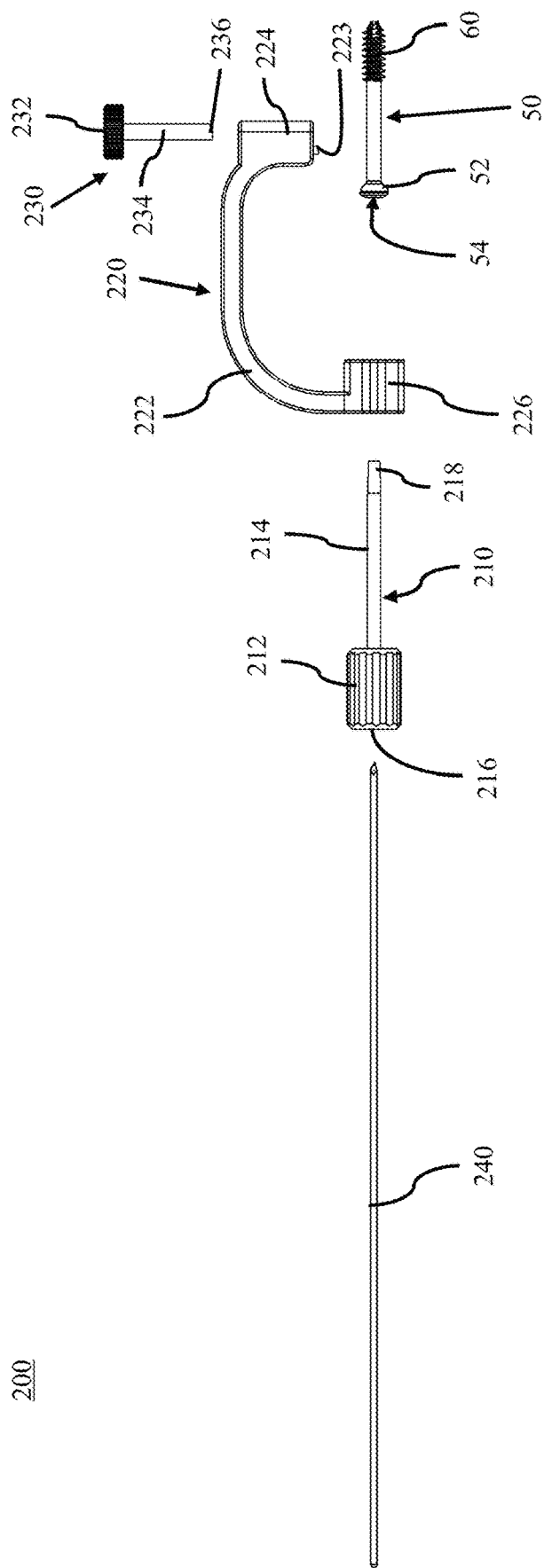
FIG. 10 is an exploded side view of the bone plate alignment guide apparatus of FIG. 9, in accordance with an aspect of the present invention.
Figure 11:
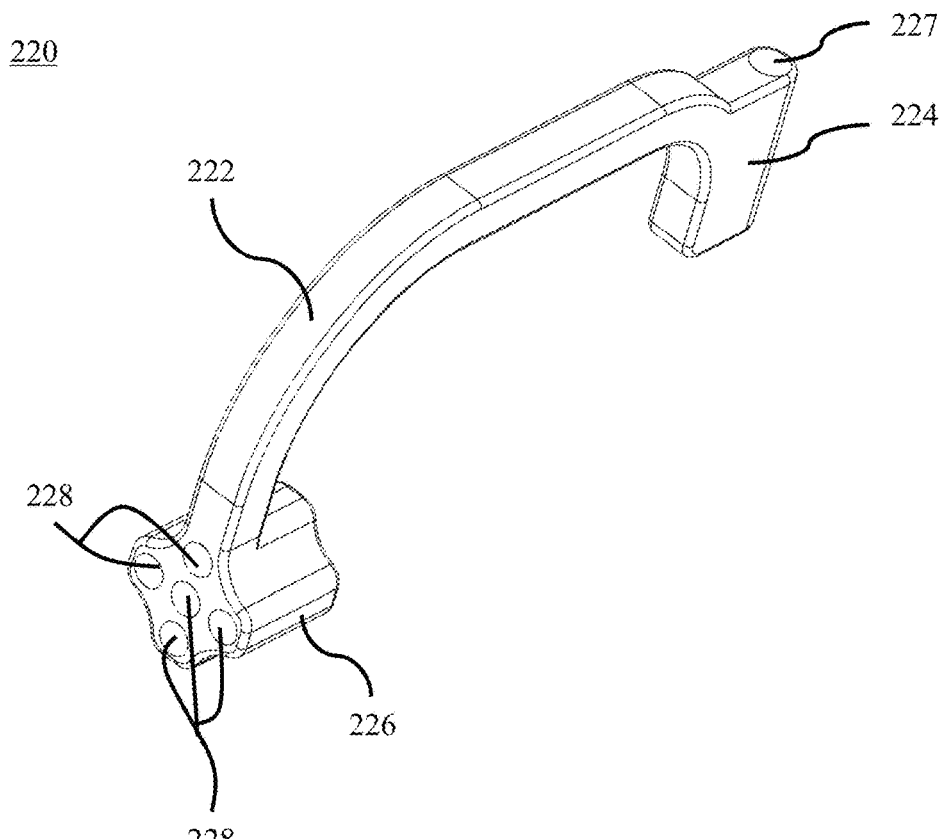
FIG. 11 is an end perspective view of the body of the bone plate alignment guide apparatus of FIG. 9, in accordance with an aspect of the present invention.
Figure 12:
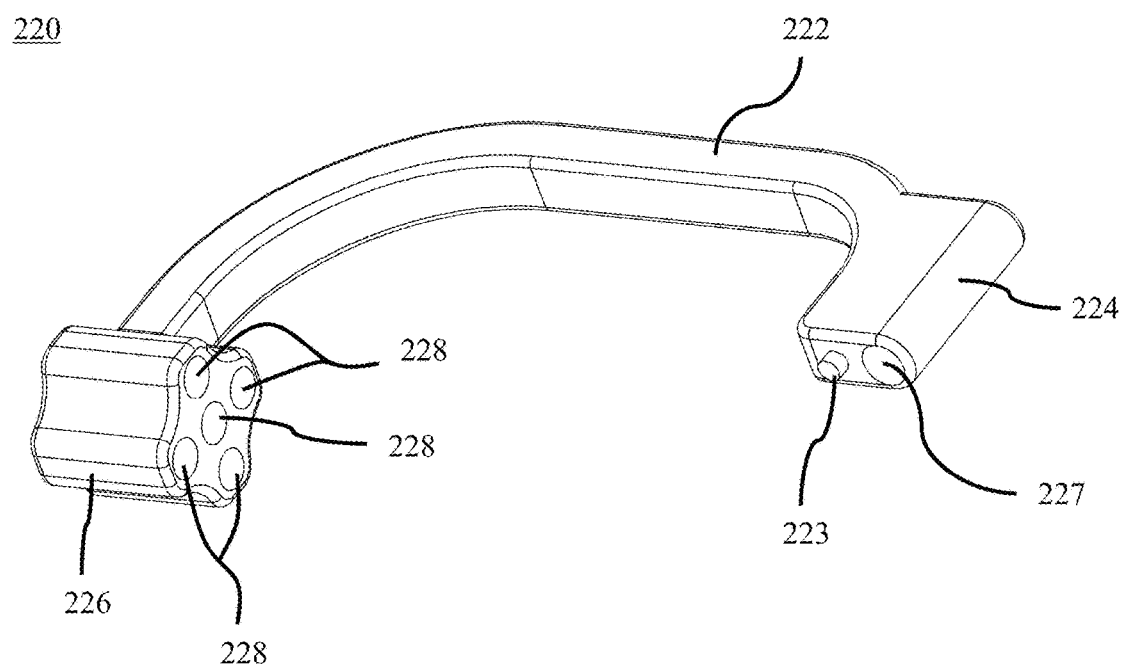
FIG. 12 is a bottom perspective view of the body of FIG. 11, in accordance with an aspect of the present invention.

The guide pin tissue protector 210, as shown in FIG. 10, may include a handle portion 212 at a first end and a shaft 214 extending away from the handle portion 212 to a tip 218 at a second end. The guide pin tissue protector 210 may also include a through hole 216 extending from the first end to the second end to enable a guide wire 240 to pass through the tissue protector 210.

As shown in FIGS. 9-12, the body 220 may include an arm 222 with an attachment portion 224 at a first end and an alignment portion 226 at a second end. The alignment portion 226 of the body 220 may be, for example, a variable hole alignment portion, and may include a plurality of holes 228. The plurality of holes 228 may include a center hole, a top hole above the center hole, a bottom hole below the center hole, a right hole to the right of the center hole, and a left hole to the left of the center hole. The plurality of holes 228 may be angled to a desired insertion angle relative to the arm 222 of the body 220. By way of specific example, the top hole, bottom hole, left hole, and right hole may each be slightly angled toward the center hole such that each of the outer holes slightly converge toward the center hole. The body 220 may also include a through hole 227 in the attachment portion 224 of the body 220. The body 220 may also include an alignment protrusion 223 extending away from the attachment portion 224 for engaging an opening in the bone plate 80. The alignment protrusion 223 may be used to position the bone plate alignment guide apparatus 200 on the bone plate 80, as shown in FIGS. 13-15.

As shown in FIGS. 13-18, a method for using the bone plate alignment guide apparatus 200 is shown. The body 220 of the alignment guide apparatus 200 may be secured to the bone plate 80 prior to aligning the plate 80 on the patient's bones. The body 220 of the alignment guide apparatus 200 may be secured to the plate 80 by inserting the alignment protrusion 223 into the first opening 96 in the plate 80 and also by inserting the fixation member 230 through the attachment portion 224 of the body 220 to engage the second opening 98 in the plate 80. Specifically, the engagement portion 236 may be coupled to the second opening 98 in the bone plate 80.

Figure 13:
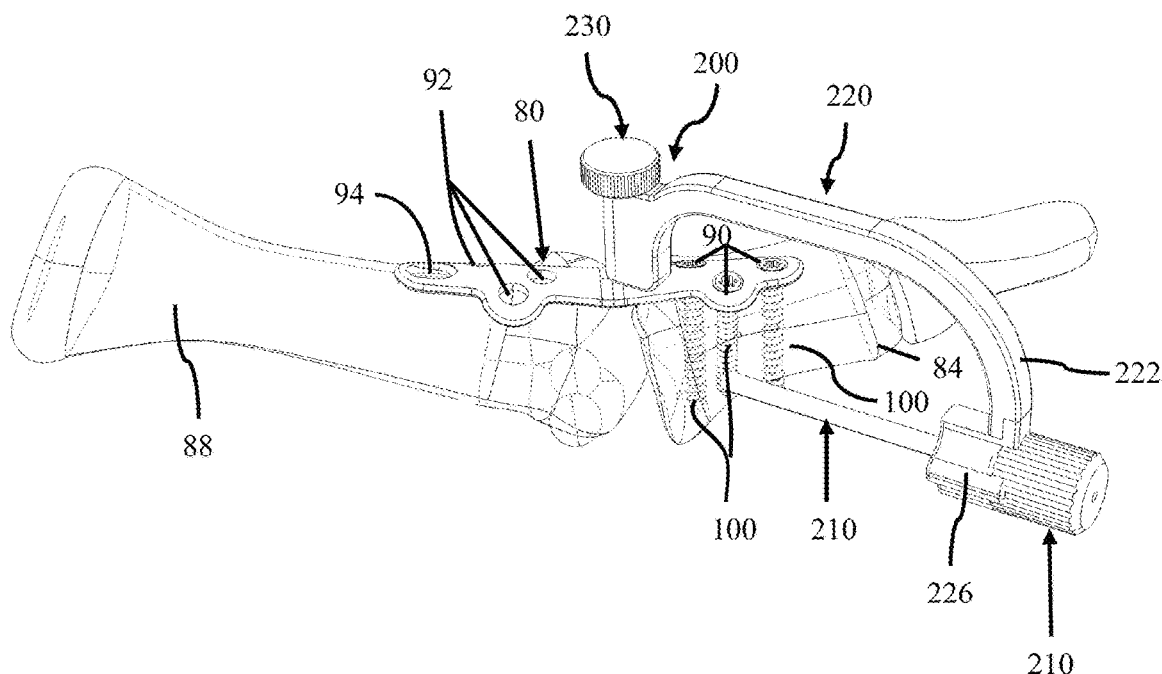
FIG. 13 is a side view of the bone plate alignment guide apparatus and the guide pin tissue protector of FIG. 9 for use in inserting a fastener into the patient's bones, in accordance with an aspect of the present invention.

The bone plate 80 with the attached alignment guide apparatus 200 may then be aligned over the patient's bones 84, 88, as shown in FIG. 13. The alignment markings 87 on the plate 80 may be used to assist the surgeon in aligning the plate 80 on the patient's bones 84, 88. Next, at least one temporary fixation device may be inserted to secure the bone plate 80 to the patient's bones 84, 88. The temporary fixation devices (Not Shown) may be inserted, for example, into at least one through hole 90 in the first end 82 of the plate 80 and into the compression slot 94 in the second end 86 of the plate 80. Alternatively, as shown in FIG. 13, fasteners 100 may be inserted into the first end 82 of the plate 80 and at least one temporary fixation device, now shown, may be inserted into the compression slot 94 in the second end 86 of the plate 80. The first end 82 of the plate 80 may be the distal end of the plate 80 while the second end 86 of the plate 80 may be the proximal end of the plate 80. Once the plate 80 is positioned and secured, at least temporarily, to the bones 84, 88, then the guide pin tissue protector 210 may be inserted into one of the plurality of holes 228 in the alignment portion 226, as shown in FIG. 13.

Figure 14:
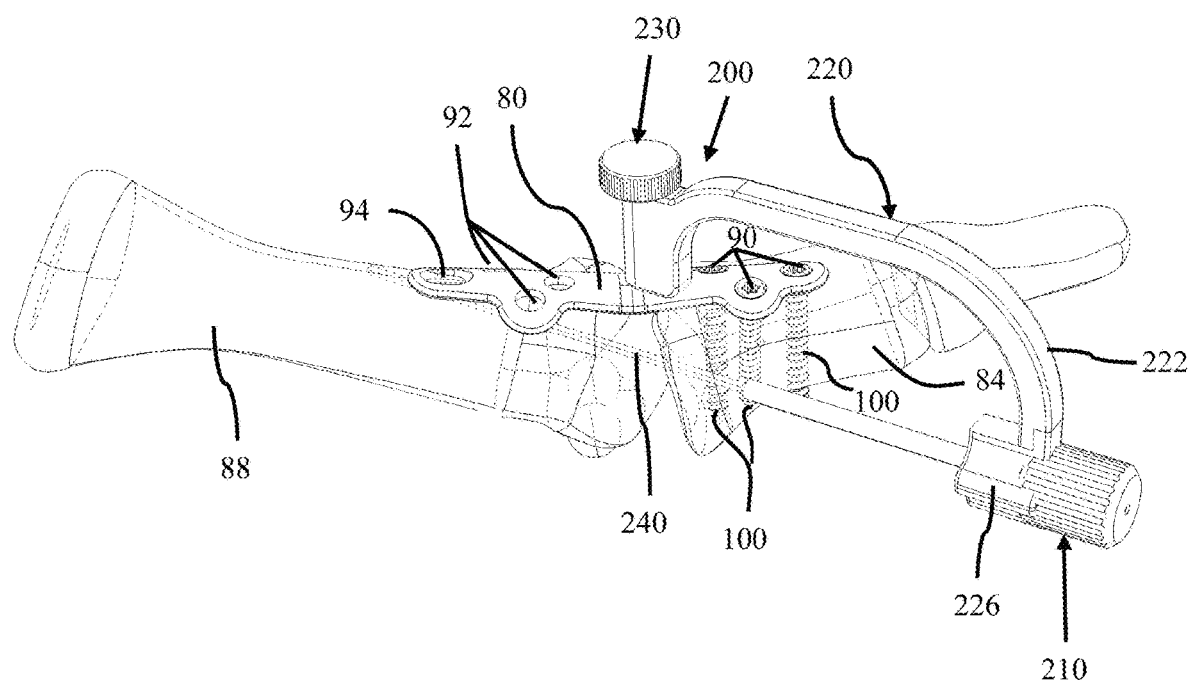
FIG. 14 is a side view of the bone plate alignment guide, guide pin tissue protector, and guide pin of FIG. 9 being used to insert a fastener into a patient's bones, in accordance with an aspect of the present invention.
Figure 15:
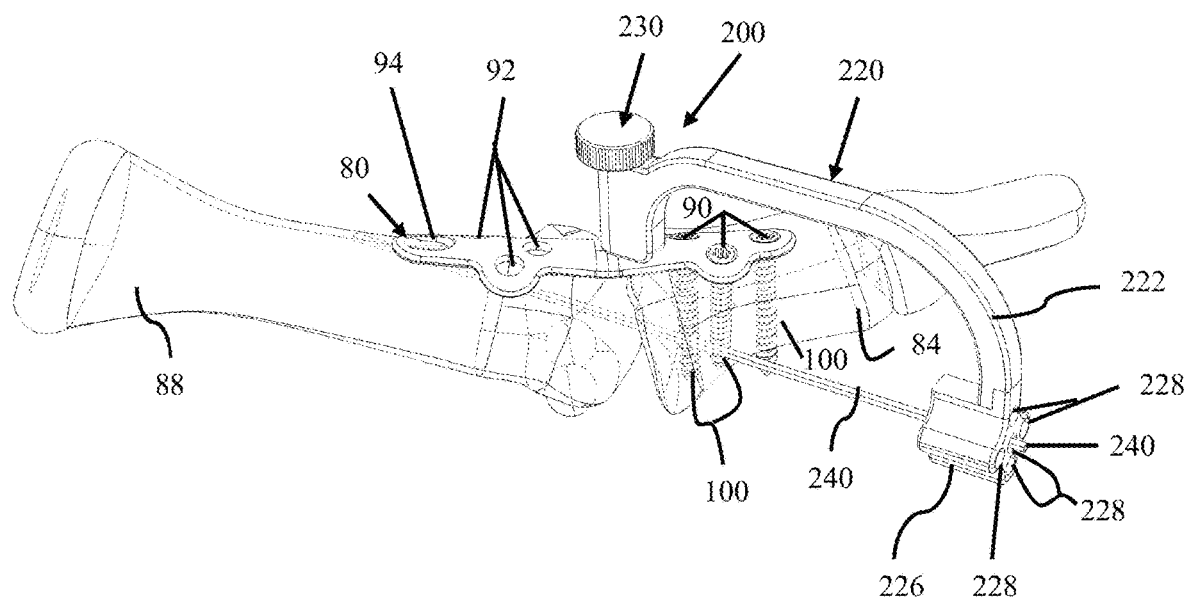
FIG. 15 is a side view of the bone plate alignment guide and guide pin of FIG. 9 being used to insert a fastener into a patient's bones, in accordance with an aspect of the present invention.
Figure 16:
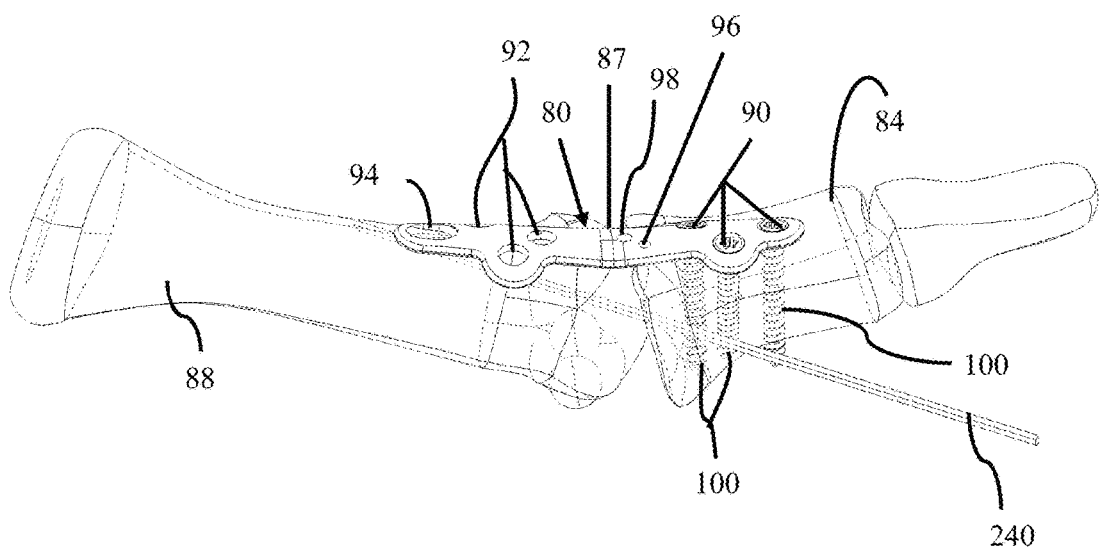
FIG. 16 is a side view of the patient's bones after removal of the bone plate alignment guide of FIG. 9 with the guide pin of FIG. 9 inserted across the patient's joint, in accordance with an aspect of the present invention.

As shown in FIG. 14, the guide wire 240 may then be inserted through the tissue protector 210 and into the bones 84, 88 across the joint. After the guide wire 240 is inserted into the bones 84, 88 in a desired position, the tissue protector 210 may be removed from the alignment portion 226 of the body 220, as shown in FIG. 15. Next, a drill may be inserted through the alignment portion 226 and over the guide wire 240 to drill an opening (Not Shown) into the bones 84, 88 across the joint. After the opening is drilled, the drill may be removed and then the body 220 of the alignment guide apparatus 200 may be removed, as shown in FIG. 16. The body 220 of the alignment guide apparatus 200 may be removed by loosening the fixation member 230 to disengage the engagement portion 236 from the second opening 98 in the plate 80.

Figure 17:
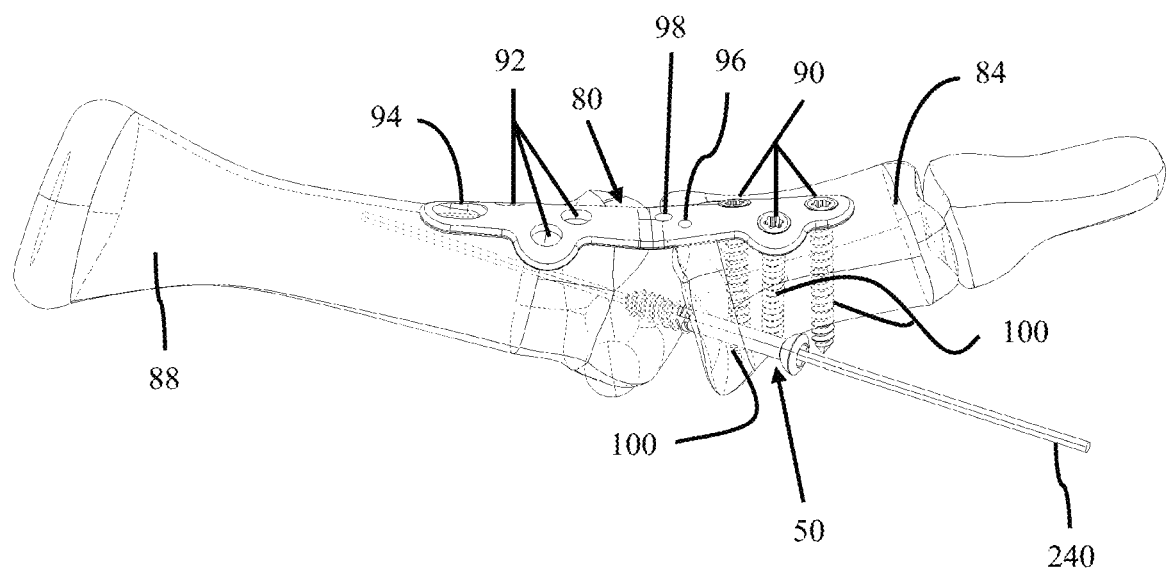
FIG. 17 is a side view of the patient's bones with a fastener partially inserted into the bones over the guide pin of FIG. 9, in accordance with an aspect of the present invention.
Figure 18:
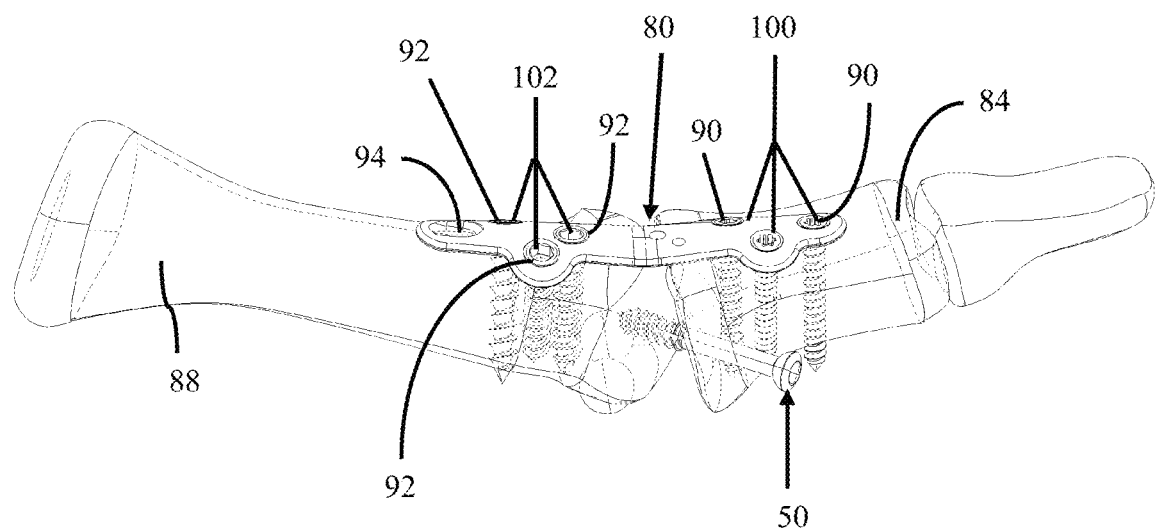
FIG. 18 is a side view of the patient's bones with a fastener inserted across the patient's joint after removal of the guide pin of FIG. 9, in accordance with an aspect of the present invention.

Next, as shown in FIG. 17, a fastener 50 may be inserted over the guide wire 240 and into the opening (Not Shown) in the bones 84, 88 across the joint. As the fastener 50 is inserted into the opening in the bones 84, 88, the bones 84, 88 will move or compress to decrease the joint space between the first bone 84 and the second bone 88. Then the guide wire 240 may be removed as shown in FIG. 18. The temporary fixation device (Not Shown) in the compression slot 94 may then be removed and at least one fastener 102 may be inserted into at least one through hole 92 to secure the second end 86 of the plate 80 to the second bone 88. After the plate is secured to the bones 84, 88 at the first end 82 and second end 86 of the plate 80 and the fastener 50 has been inserted across the joint space, the patient's incision may be closed.

Figure 19:
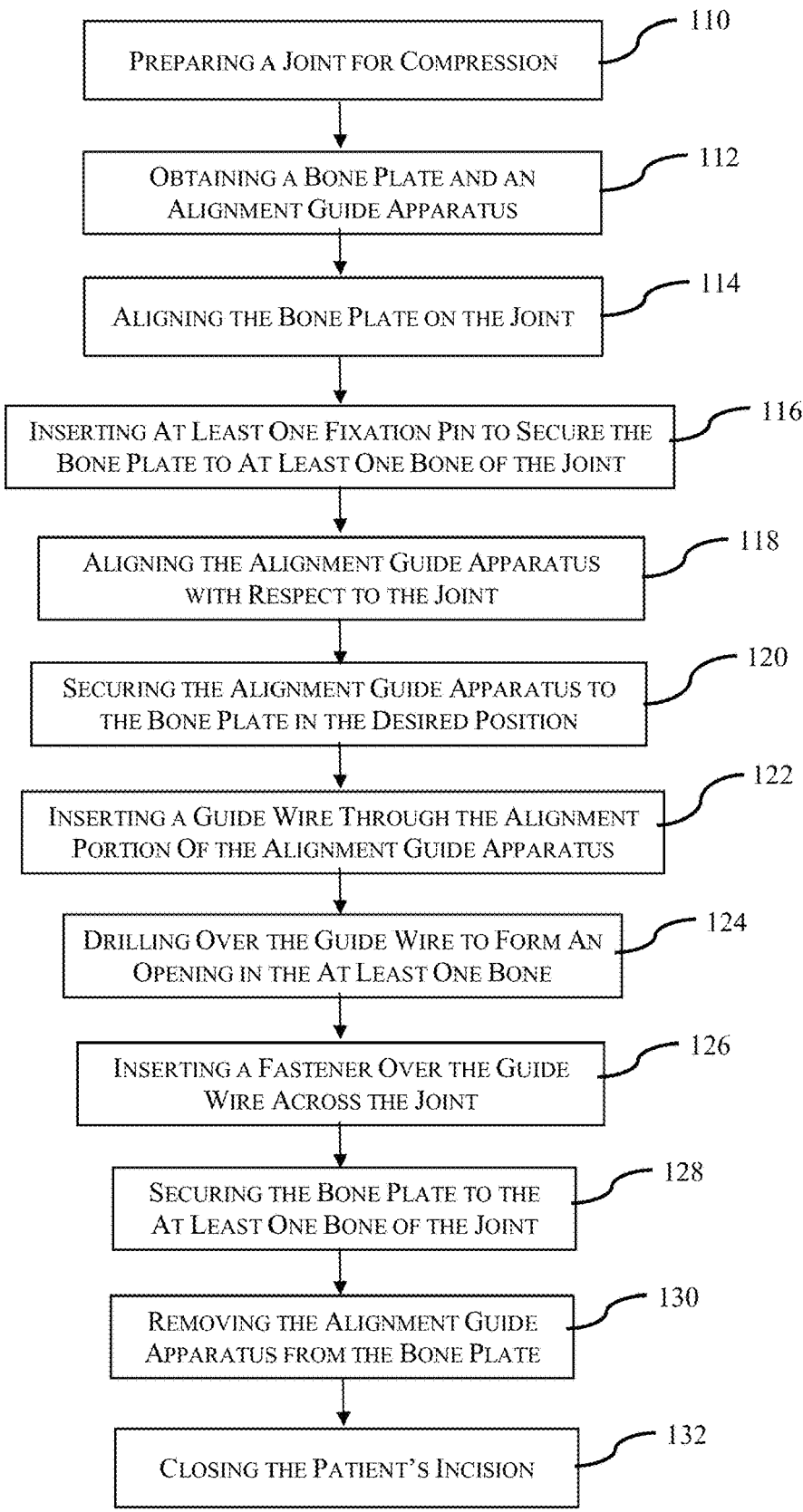
FIG. 19 depicts one embodiment of a method for compressing a joint, in accordance with an aspect of the present invention.
Figure 20:
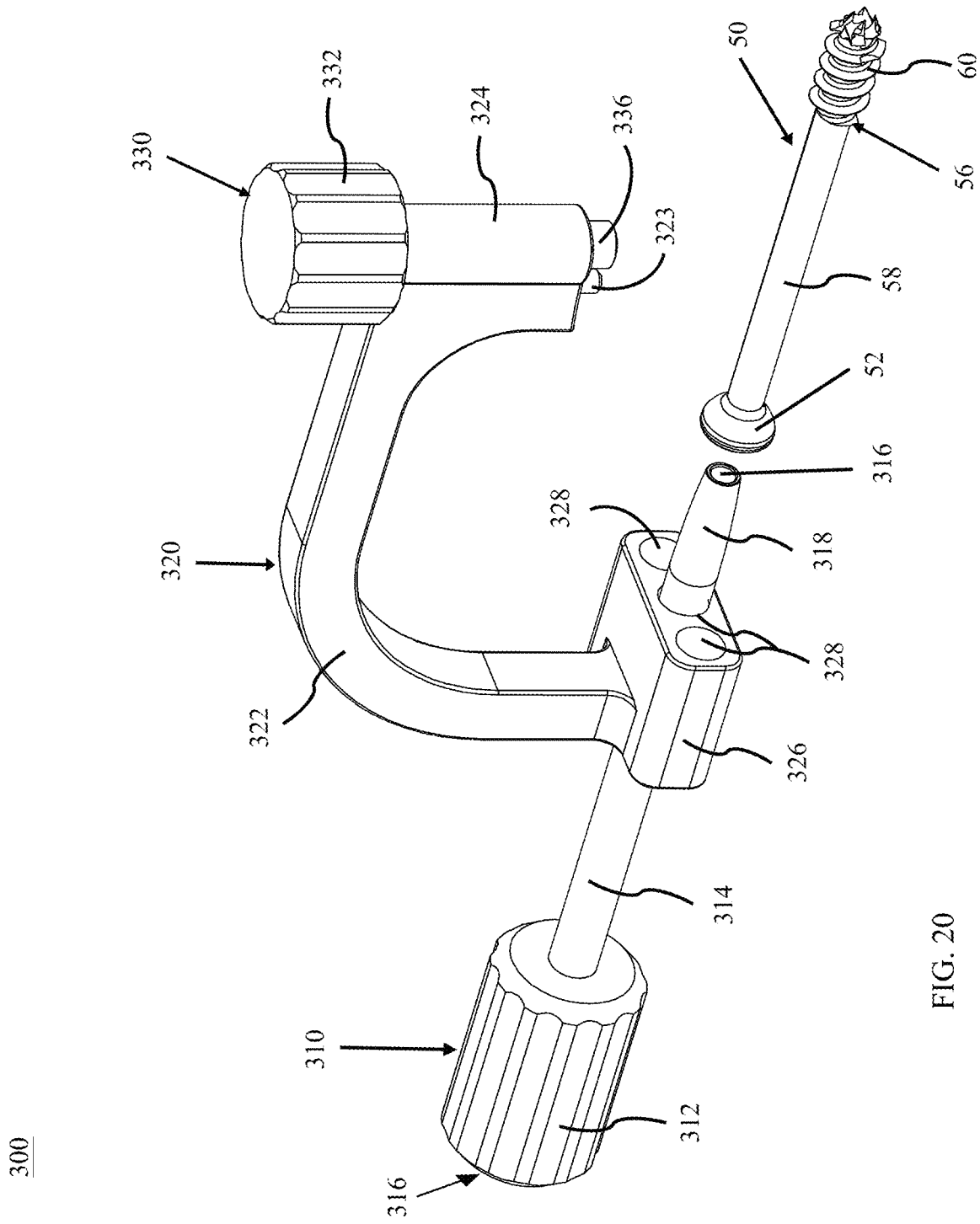
FIG. 20 is a perspective view of a bone plate alignment guide apparatus, in accordance with an aspect of the present invention.
Figure 21:
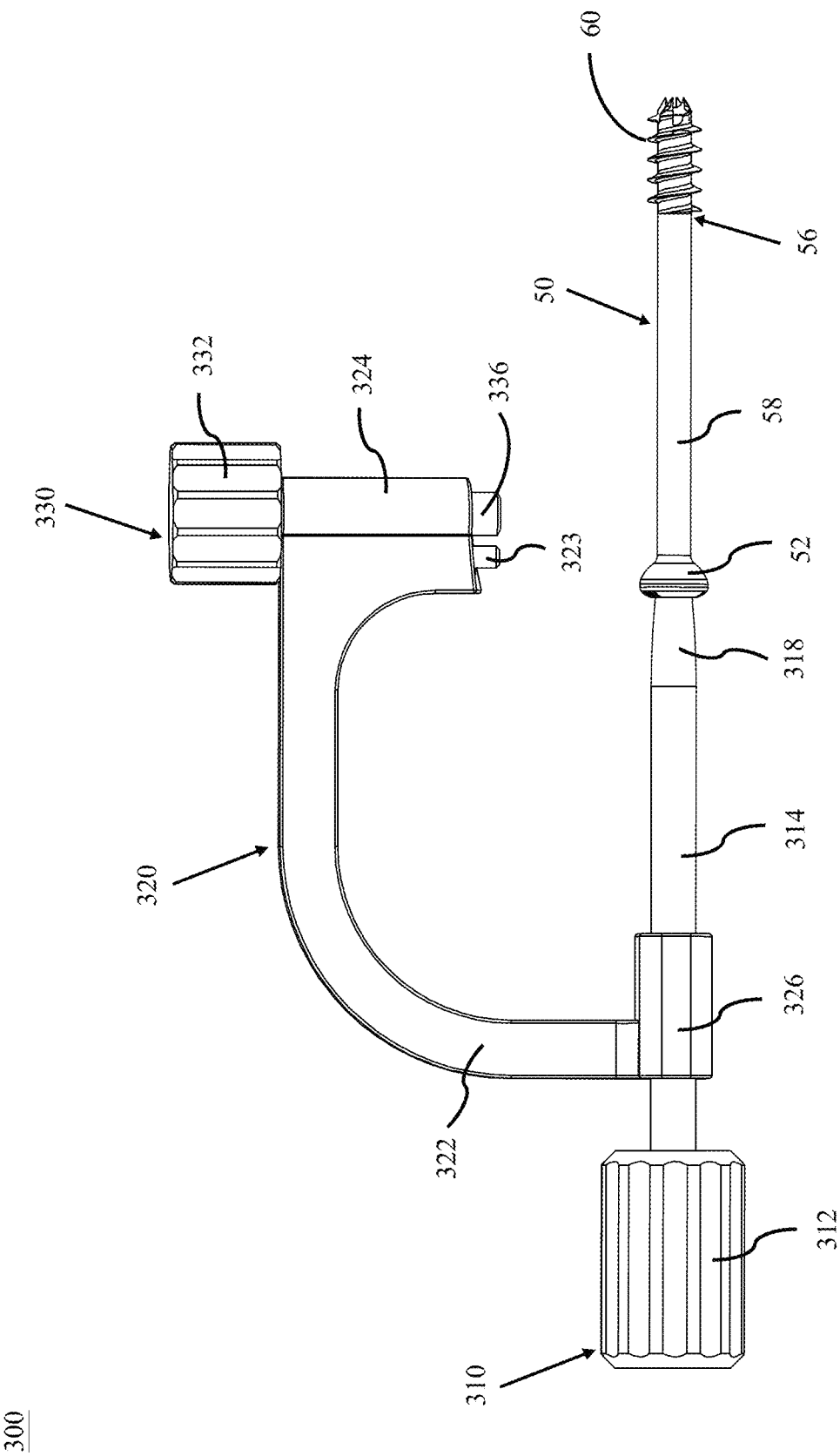
FIG. 21 is a side view of the bone plate alignment guide apparatus of FIG. 20, in accordance with an aspect of the present invention.

Referring now to FIG. 19, another method for using a bone plate alignment guide apparatus 10, 200 is illustrated. As shown in FIG. 19, the method may include, for example, preparing a joint for compression 110. The method may further include obtaining a bone plate and an alignment guide apparatus 112 and aligning the bone plate on the joint 114. The method may also include inserting at least one fixation pin to secure the bone plate to at least one bone of the joint 116 and aligning the alignment guide apparatus with respect to the joint 118. Further, the method may include securing the alignment guide apparatus to the bone plate in the desired position 120 and inserting a guide wire through the alignment portion of the alignment guide apparatus 122. The method may also include drilling over the guide wire to form an opening in the at least one bone 124 and inserting a fastener over the guide wire across the joint 126. In addition, the method may include securing the bone plate to at least one bone of the joint 128 and removing the alignment guide apparatus from the bone plate 130. Finally, the method may include closing the patient's incision 132.

Another bone plate alignment guide apparatus 300 is shown in FIGS. 20-24. The bone plate alignment guide apparatus 300 may include a body or alignment guide 320, a fixation member 330, a guide pin tissue protector 310, a guide wire or pin (not shown), and a fastener 50. The fixation member 330 may include a knob portion 332 and a shaft portion 334 with an engagement portion 336 for engaging a bone plate, for example, bone plate 80 of FIG. 5. The engagement portion 336 may be, for example, threaded to engage corresponding threads in an opening in a bone plate, deformable to be removeably press fit into the opening in the bone plate, or similar configurations that achieve a coupling of the guide apparatus 300 to a bone plate. The guide wire (not shown) may be of the type described above with reference to guide wire 240, which will not be described again here for brevity sake. The fastener 50 may be of the type described above with reference to FIGS. 1-5 and includes, for example, a compression screw, lag screw, headless screw, or a solid screw, which will also not be described again here for brevity sake.

Figure 22:
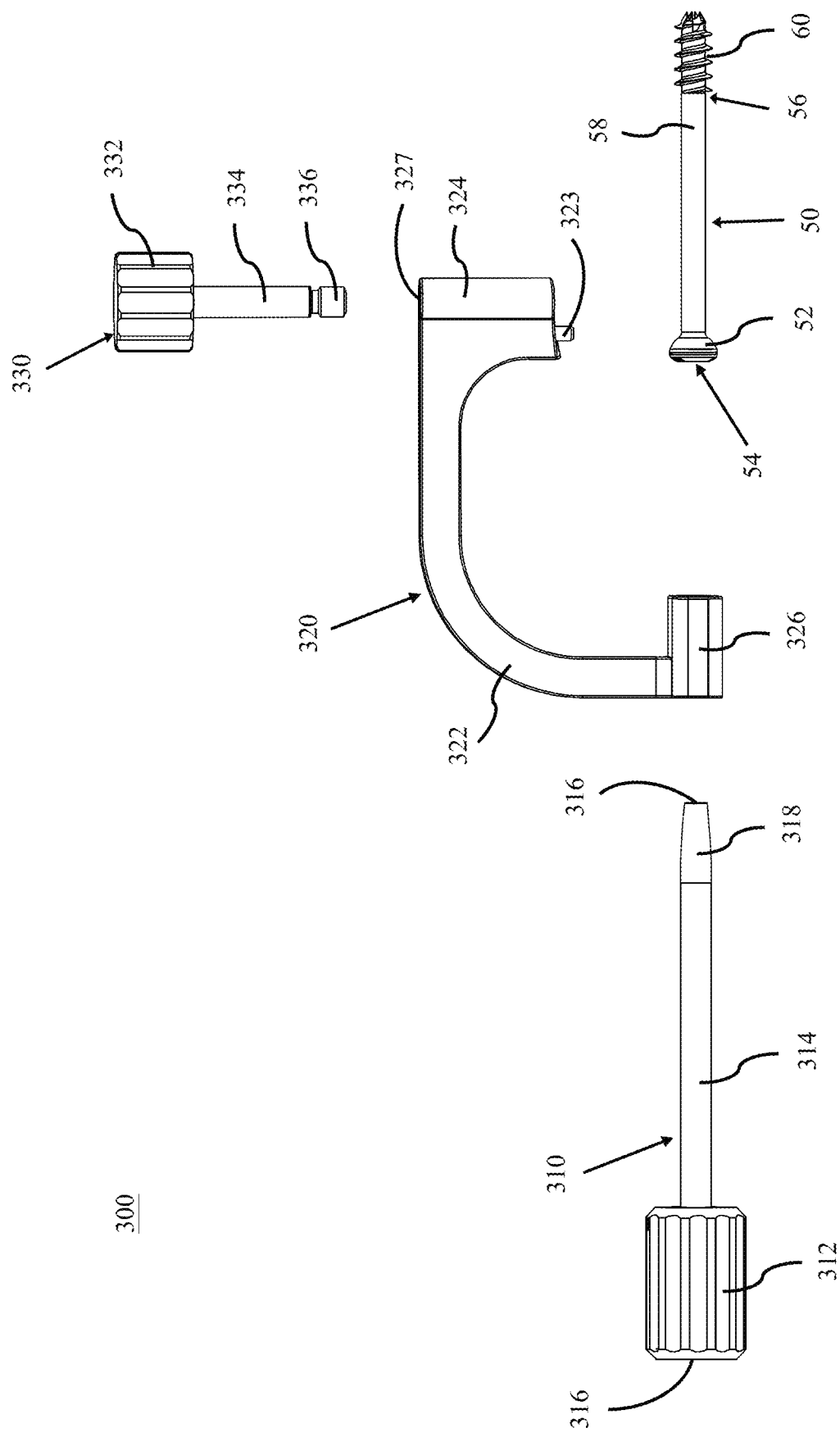
FIG. 22 is an exploded side view of the bone plate alignment guide apparatus of FIG. 20, in accordance with an aspect of the present invention.

The guide pin tissue protector 310, as shown in FIG. 22, may include a handle portion 312 at a first end and a shaft 314 extending away from the handle portion 312 to a tip 318 at a second end. The shaft 314 may taper at the second end to form the tip 318. The guide pin tissue protector 310 may also include a through hole 316 extending from the first end to the second end to enable a guide wire (not shown) to pass through the tissue protector 310 and engage the patient's bone.

Figure 23:
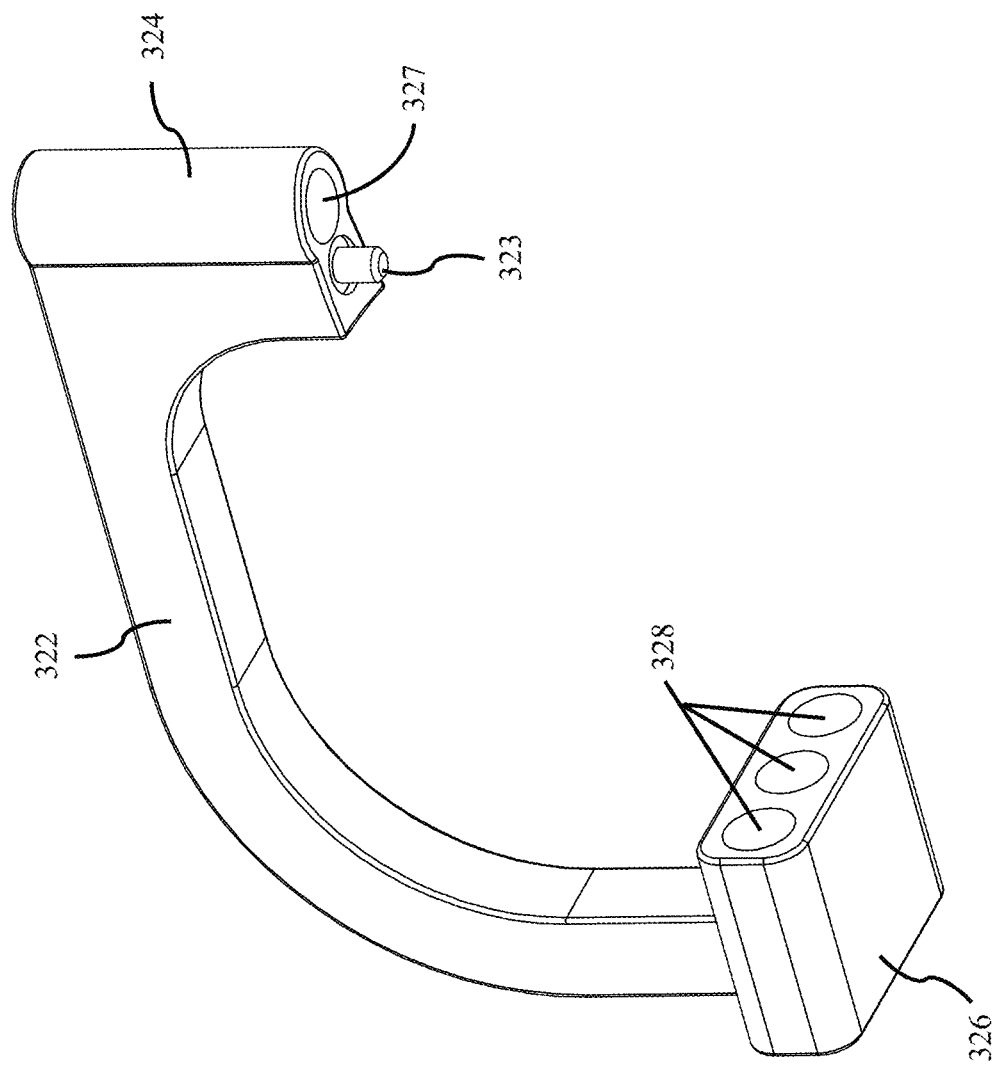
FIG. 23 is a bottom perspective view of the body of the bone plate alignment guide apparatus of FIG. 20, in accordance with an aspect of the present invention.
Figure 24:
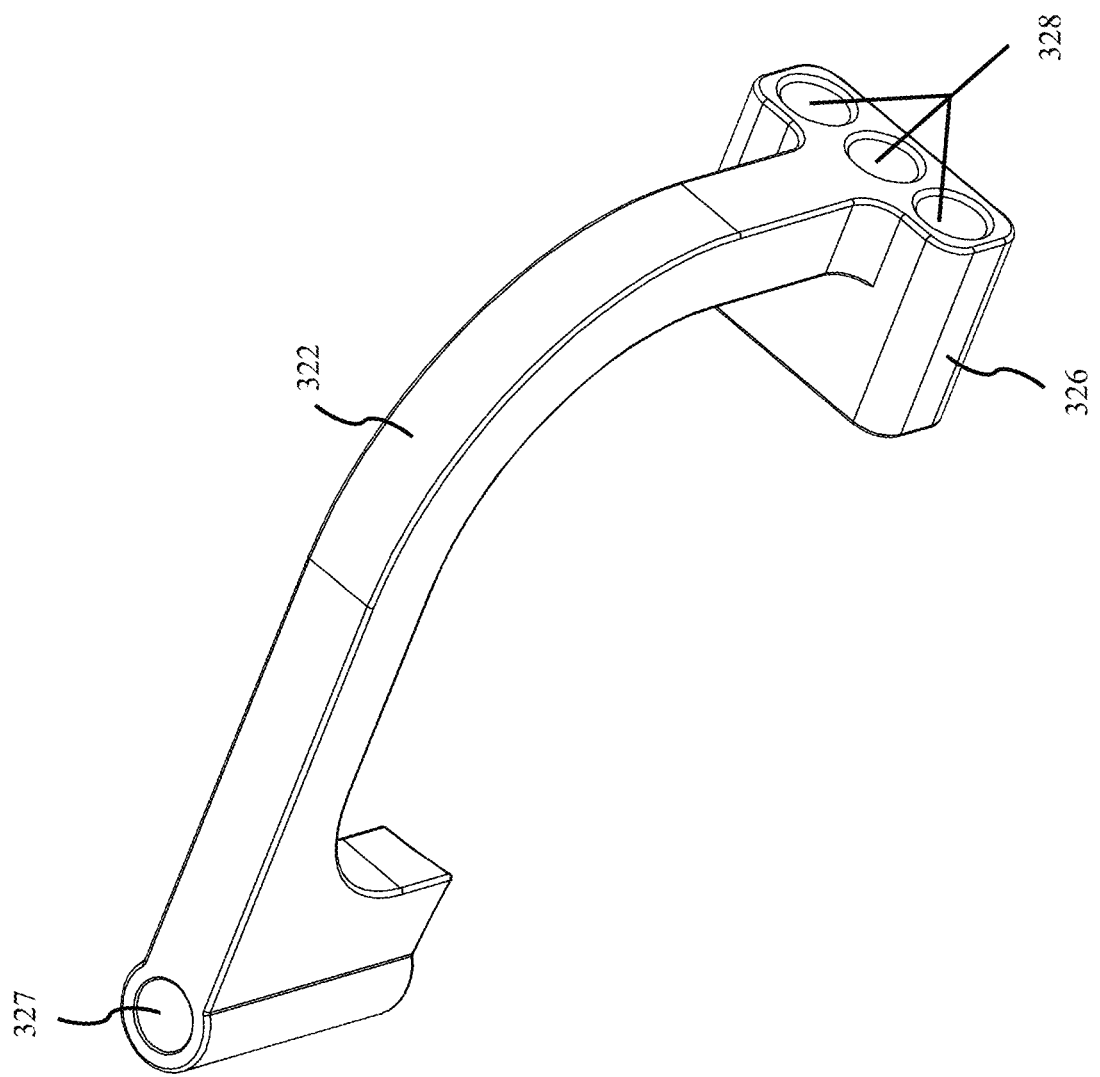
FIG. 24 is an end perspective view of the body of the bone plate alignment guide apparatus of FIG. 20, in accordance with an aspect of the present invention.

As shown in FIGS. 20-24, the body 320 may include an arm 322 with an attachment portion 324 at a first end and an alignment portion 326 at a second end. The alignment portion 326 of the body 320 may be, for example, a variable hole alignment portion, and may include a plurality of holes 328. The plurality of holes 328 may be positioned in a linear arrangement with a center hole, a right hole to the right of the center hole, and a left hole to the left of the center hole. The plurality of holes 328 may be straight or angled to a desired insertion position relative to the arm 322 of the body 320. By way of specific example, the left hole and right hole may each be slightly angled toward the center hole such that each of the side holes converge toward the center hole. The body 320 may also include a through hole 327 in the attachment portion 324 of the body 320, as seen in FIGS. 23-24. Further, the body 320 may include an alignment protrusion 323 extending away from the attachment portion 324, as shown in FIGS. 20-23, for engaging an opening in a bone plate, such as bone plate 80 of FIG. 5. The alignment protrusion 323 may be used to position the bone plate alignment guide apparatus 300 on a bone plate.

The method for using a bone plate alignment guide apparatus, as described above with reference to FIG. 19, may also be performed using the bone plate alignment guide apparatus 300.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. An alignment guide apparatus, comprising:
    a body, the body comprising:
        an arm with a first end and a second end;
        an attachment portion at the first end, the attachment portion comprising:
            at least one hole extending through the attachment portion along a longitudinal axis; and an alignment portion at the second end, the alignment portion comprising:
            at least one through hole extending through the alignment portion along a longitudinal axis;
    a fixation insert slidingly connected to the attachment portion;
    a guide pin slidingly engaged to the alignment portion; and
    a screw configured to engage the guide pin;
    wherein the at least one hole of the attachment portion receives the fixation insert;
    wherein the at least one through hole of the alignment portion receives the guide pin; and
    wherein the at least one through hole of the alignment portion comprises a plurality of holes which extend through the alignment portion.

2. The alignment guide apparatus of claim 1, wherein the plurality of holes comprises three holes.

3. The alignment guide apparatus of claim 2, wherein the three holes include a central hole and two holes positioned linearly with the central hole and define a right hole and a left hole.

4. The alignment guide apparatus of claim 3, wherein at least one of the right hole and left hole are angled towards the central hole.

5. The alignment guide apparatus of claim 3, wherein the right hole and left hole are angled towards the central hole, wherein a central axis for each of the right hole and left hole intersect a central axis of the central hole at a distance from the alignment portion.

6. The alignment guide apparatus of claim 3, wherein the arm is configured to position the through hole of the attachment portion generally perpendicular to the at least one through hole of the alignment portion.

7. The alignment guide apparatus of claim 1, wherein the plurality of holes may be at least one of straight and angled relative to the alignment portion.

8. The alignment guide apparatus of claim 1, wherein the fixation insert comprises:
    a knob portion; and
    a shaft portion extending away from the knob portion.

9. The alignment guide apparatus of claim 7, wherein the shaft portion comprises an alignment portion and a threaded section.

10. The alignment guide apparatus of claim 1, wherein the guide pin comprises:
    a first end and a second end:
    a shaft portion having a handle portion connected to the first end;
    a tip proximate to the second end; and
    a hole extending from the first end to the second end.

11. The alignment guide apparatus of claim 1, wherein the screw has a first end and a second end, the screw comprising:
   a head portion at the first end;
   a shaft portion extending away from the head portion to the second end, wherein the shaft portion comprises a smooth portion and a threaded portion; and
   a through hole extending from the first end to the second end.

12. A bone plate, comprising:
   a first end;
   a second end; and
   an intermediate portion connecting the first end and second end, the intermediate portion disposed adjacent proximal portions of the first and second ends;
   at least one first through hole near the first end, wherein the at least one first through hole comprises three through holes disposed between a distal portion of the first end and the proximal portion of the first end;
   at least one second through hole near the second end, wherein the at least one second through hole comprises a pair of through holes disposed between a distal portion of the second end and the proximal portion of the second end;
   at least one compression slot positioned on the second end and disposed between the at least one second through hole and the distal portion of the second end; and
   at least one opening between the first end and the second end, wherein the at least one opening comprises:
      a first opening; and
      a second opening;
      wherein the first opening and the second opening are positioned in the intermediate portion, wherein the first opening is offset from the second opening relative to a longitudinal axis which extends from the first end to the second end, wherein the first opening is offset from the second opening relative to a lateral axis which extends from a first side surface to a second side surface of the bone plate, and wherein the first and second openings are configured for aligning a guide relative to the bone plate and at least one bone in an insertion position.

13. The bone plate of claim 12, wherein the intermediate portion comprises:
   at least one alignment marking.

14. The bone plate of claim 13, wherein the at least one alignment marking comprises:
   three alignment markings.

15. The bone plate of claim 13, wherein at least one of the at least one opening between the first and second ends overlaps at least one of the at least one alignment marking.

16. The bone plate of claim 12, wherein the three through holes are positioned spaced apart from each other around the first and second side surfaces of the first end.

17. The bone plate of claim 16, wherein each of the three through holes are positioned in a lobe extending away from the first and second side surfaces of the first end.

18. The bone plate of claim 12, wherein the pair of through holes are positioned spaced apart from each other around the first and second side surfaces of the second end.

19. The bone plate of claim 12, wherein each of the two holes of the pair of through holes and the compression slot are positioned in a lobe extending away from the first and second side surfaces of the second end.

* * * * *

UNITED STATES PATENT AND TRADEMARK OFFICE
CERTIFICATE OF CORRECTION

PATENT NO. : 11,395,691 B2
APPLICATION NO. : 16/450505
DATED : July 26, 2022
INVENTOR(S) : Dacosta et al.

Page 1 of 1

It is certified that error appears in the above-identified patent and that said Letters Patent is hereby corrected as shown below:

In the Claims

Column 10, Line 58: Claim 9, Delete "claim 7" and insert -- claim 8 --

Signed and Sealed this
Thirtieth Day of August, 2022

Katherine Kelly Vidal
*Director of the United States Patent and Trademark Office*